(12) United States Patent
Ito et al.

(10) Patent No.: US 12,085,708 B2
(45) Date of Patent: Sep. 10, 2024

(54) IMAGE PICKUP APPARATUS MANUFACTURING METHOD AND IMAGE PICKUP APPARATUS

(71) Applicant: OLYMPUS CORPORATION, Tokyo (JP)

(72) Inventors: Yuki Ito, Ina (JP); Yusuke Nakagawa, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 451 days.

(21) Appl. No.: 17/411,411

(22) Filed: Aug. 25, 2021

(65) Prior Publication Data
US 2021/0382294 A1    Dec. 9, 2021

Related U.S. Application Data

(63) Continuation of application No. PCT/JP2019/015656, filed on Apr. 10, 2019.

(51) Int. Cl.
*G02B 23/24* (2006.01)
*A61B 1/00* (2006.01)
(Continued)

(52) U.S. Cl.
CPC ........ *G02B 23/2484* (2013.01); *A61B 1/0011* (2013.01); *G02B 3/0012* (2013.01);
(Continued)

(58) Field of Classification Search
CPC .................. A61B 1/00096; A61B 1/00; B29L 2011/0016; H04N 23/55; H04N 23/57; H01L 27/14625
(Continued)

(56) References Cited

U.S. PATENT DOCUMENTS 7,546,010 B2 * 6/2009 Fujii .................... G02B 6/4206
385/33
2008/0304525 A1 * 12/2008 Kupisiewicz .......... B41M 5/262
347/225
(Continued)

FOREIGN PATENT DOCUMENTS

JP    H11-307941 A    11/1999
JP    2001-052990 A    2/2001
(Continued)

OTHER PUBLICATIONS

International Search Report dated Jul. 9, 2019 received in PCT/JP2019/015656.

*Primary Examiner* — Alison L Hindenlang
*Assistant Examiner* — Steven S Lee
(74) *Attorney, Agent, or Firm* — Scully, Scott, Murphy & Presser, P.C.

(57) ABSTRACT

An image pickup apparatus manufacturing method includes: modifying glass inside a glass block using a laser to produce a first modified space including a first path connected to an exterior surface of the glass block; etching the first modified space to produce an optical member that internally includes an optical space including a lens surface and connected to a first hole including an opening in the exterior surface; and installing, on the optical member, an image pickup member configured to receive a subject image formed by light condensed by the optical member.

9 Claims, 9 Drawing Sheets

(51) Int. Cl.
  *G02B 3/00* (2006.01)
  *H04N 23/50* (2023.01)
  *H04N 23/54* (2023.01)
  *H04N 23/55* (2023.01)

(52) U.S. Cl.
  CPC ........... *G02B 23/243* (2013.01); *H04N 23/54* (2023.01); *H04N 23/55* (2023.01); *A61B 1/00096* (2013.01); *H04N 23/555* (2023.01)

(58) Field of Classification Search
  USPC .......................................................... 65/37
  See application file for complete search history.

(56) References Cited

U.S. PATENT DOCUMENTS

| | | | | |
|---|---|---|---|---|
| 2009/0268304 | A1* | 10/2009 | Lin | G02B 9/12 |
| | | | | 359/642 |
| 2012/0008934 | A1* | 1/2012 | Kawasaki | H04N 23/54 |
| | | | | 156/247 |
| 2017/0059848 | A1* | 3/2017 | Haraguchi | G02B 23/2469 |
| 2017/0351156 | A1* | 12/2017 | Imai | G02B 19/0014 |

FOREIGN PATENT DOCUMENTS

| | | | | | |
|---|---|---|---|---|---|
| JP | 2003248156 | A | * | 9/2003 | ........... B29C 43/021 |
| JP | 2004087718 | A | * | 3/2004 | |
| JP | 2004223586 | A | * | 8/2004 | ........... B23K 26/382 |
| JP | 2008-109026 | A | | 5/2008 | |
| JP | 2011-242240 | A | | 12/2011 | |
| JP | 2012-018993 | A | | 1/2012 | |
| JP | 2018-168048 | A | | 11/2018 | |
| JP | 6498860 | B2 | * | 4/2019 | |
| WO | WO-2009096460 | A1 | * | 8/2009 | ........... G02B 13/003 |
| WO | 2012/017857 | A1 | | 2/2012 | |
| WO | WO-2017073440 | A1 | * | 5/2017 | ......... A61B 1/00096 |
| WO | WO-2017203592 | A1 | * | 11/2017 | ............... A61B 1/00 |
| WO | WO-2017216898 | A1 | * | 12/2017 | ......... A61B 1/00096 |
| WO | WO-2018037551 | A1 | * | 3/2018 | ......... A61B 1/00013 |

* cited by examiner

IMAGE PICKUP APPARATUS MANUFACTURING METHOD AND IMAGE PICKUP APPARATUS

CROSS REFERENCE TO RELATED APPLICATION

This application is a continuation application of PCT/JP2019/015656 filed on Apr. 10, 2019, the entire contents of which are incorporated herein by this reference.

BACKGROUND OF THE INVENTION

1. Field of the Invention

The present invention relates to a method of manufacturing an image pickup apparatus provided with an optical member and an image pickup member, to an image pickup apparatus provided with an optical member and an image pickup member, and to an endoscope including an image pickup apparatus provided with an optical member and an image pickup member.

2. Description of the Related Art

For an image pickup apparatus provided in an endoscope, miniaturization and a smaller diameter in particular are important for reducing invasiveness.

Japanese Patent Application Laid-Open Publication No. 2012-18993 discloses an optical member including a wafer-level stack as a method of efficiently manufacturing an optical member of an image pickup apparatus. A wafer-level optical member is produced by dicing/individualizing a stacked wafer obtained by stacking and bonding a plurality of element wafers with an adhesive, each element wafer including a plurality of optical elements.

The endoscope is used in humid environments and may be subjected to autoclaving (high-temperature and high-pressure steaming).

International Publication No. 2012/017857 discloses an electronic circuit chip in which a femtosecond laser is used to create a modified space inside a glass substrate, the modified space is melted by an etching process, and a small cavity formed as a result is filled with a conductive material.

SUMMARY OF THE INVENTION

An image pickup apparatus manufacturing method according to an embodiment of the present invention includes: modifying glass inside a glass block using a laser to produce a first modified space including a first path connected to an exterior surface of the glass block; etching the first modified space to produce an optical member that internally includes an optical space including at least one lens surface and connected to a first hole including an opening in the exterior surface; and installing, on the optical member, an image pickup member configured to receive a subject image formed by light condensed by the optical member.

An image pickup apparatus according to another embodiment of the present invention includes: an optical member including an optical space including at least one lens surface inside a glass block, the optical member including a first hole connected to the optical space, the first hole including an opening in an exterior surface of the glass block; and an image pickup member configured to receive a subject image formed by light condensed by the optical member.

An endoscope according to another embodiment of the present invention includes: an optical member including an optical space including at least one lens surface inside a glass block, the optical member including a first hole connected to the optical space, the first hole including an opening in an exterior surface of the glass block; and an image pickup member configured to receive a subject image formed by light condensed by the optical member.

DETAILED DESCRIPTION OF THE PREFERRED EMBODIMENT(S)

First Embodiment

Figure 1:
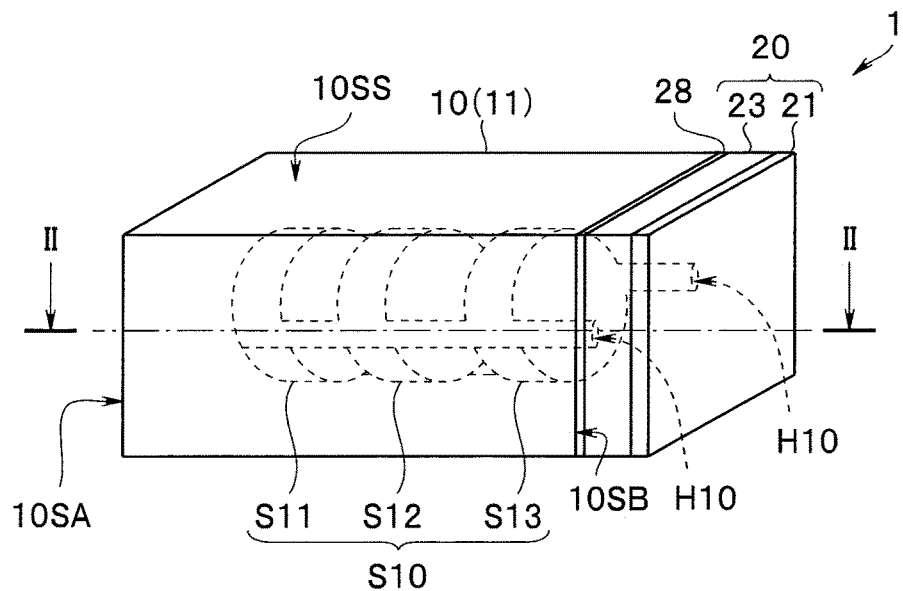
FIG. 1 is a perspective view of an image pickup apparatus according to a first embodiment.
Figure 2:
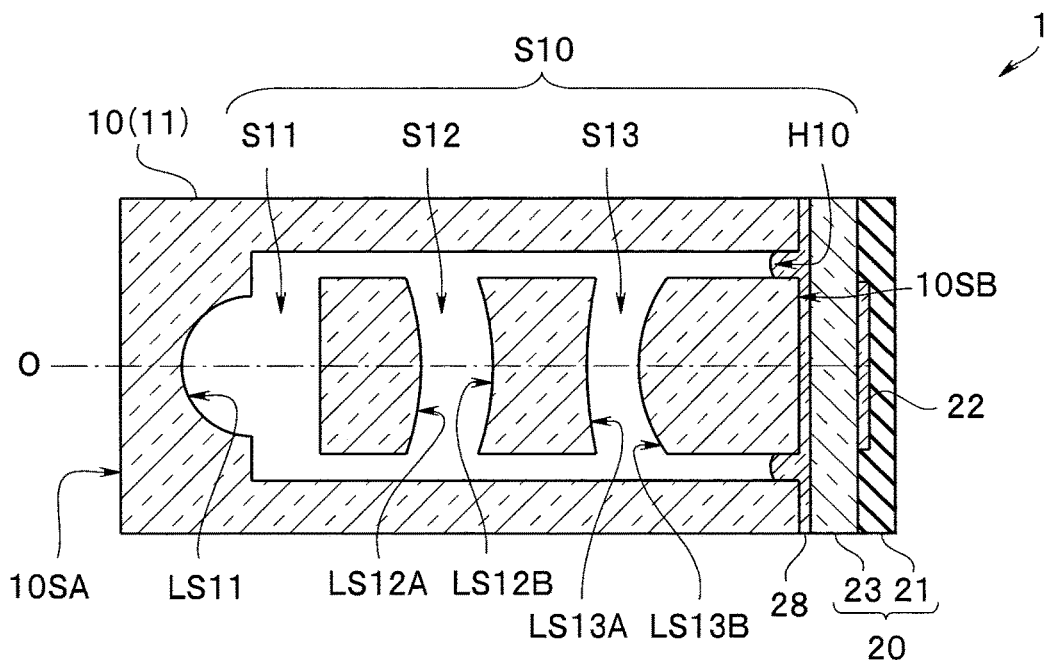
FIG. 2 is a cross section along a line II-II in FIG. 1.

As illustrated in FIGS. 1 and 2, an image pickup apparatus 1 according to the present embodiment includes an optical member 10 and an image pickup member 20. The optical member 10 and the image pickup member 20 are bonded using an adhesive 28.

Note that in the following description, the drawings based on each embodiment are schematic illustrations. Features such as the relationship between the thickness and width of each portion, the thickness ratios of respective portions, and the relative angles therebetween are different from the real features. The drawings also include portions where the dimensional relationships and ratios differ from each other. Some components are omitted from illustration.

The image pickup member 20 includes an image pickup device 21 in which is formed a light-receiving unit 22 that receives a subject image formed by light condensed by the optical member 10, and a cover glass 23 that protects the light-receiving unit 22.

The optical member 10 uses a Mass block 11 having a substantially rectangular parallelepiped shape as a substrate, the glass block 11 including an exit surface 10SB on which the image pickup member 20 is disposed, an incident surface 10SA on the opposite side from the exit surface 10SB, and four side surfaces 10SS. An optical space S10 (S11, S12, S13) having a lens surface is formed inside the glass block 11. The optical space S11 has a concave lens surface LS11 that causes incident light forming a subject image to diverge. The optical space S12 has a convex lens surface LS12A and a concave lens surface LS12B that condense incident light to form a subject image. The optical space S13 has a concave lens surface LS13A and a convex lens surface LS13B.

Note that the optical space S10 of the optical member 10 preferably has at least one concave lens surface and at least one convex lens surface to condense incident light to form a bright subject image.

The optical space S10 of the optical member 10 is connected to two first holes H10 that have respective openings in the exit surface 10SB. On the other hand, the first holes H10 do not have any openings in the incident surface 10SA and the side surfaces 10SS of the optical member 10.

The incident surface 10SA of the optical member 10 may be subjected to humid conditions when the image pickup apparatus 1 is used. However, in the image pickup apparatus 1, the incident surface 10SA of the optical member 10 is one face of the glass block 11 and does not have any openings to the first holes H10. Additionally, the side surfaces 10SS of the optical member 10 are also respective faces of the glass block 11 and do not have any seams containing an adhesive or the like.

As illustrated in FIG. 2, when the image pickup member 20 is bonded to the exit surface 10SB using the adhesive 28, the optical space S10 of the optical member 10 is sealed. In particular, the adhesive 28 is disposed to cover the openings to the first holes H10 and is provided inside the first holes H10. The adhesive 28 functions as a sealing resin that prevents moisture from intruding into the optical space S10.

Note that the optical member 10 is held by a tubular frame member such that the side surfaces 10SS loss are covered by the frame member, and in cases where moisture intrusion is not a concern, openings to the first holes H10 may also be provided in the side surfaces 10SS.

In the optical member 10, because the optical space S10 that forms an optical path is an internal space inside the glass block 11, moisture does not intrude from the incident surface 10SA or the side surfaces 10SS. Furthermore, the first holes H10 contain the adhesive 28 not only at the openings but also internally. The image pickup apparatus 1 has excellent moisture resistance, and degraded optical properties due to internal fogging inside the optical member are not a concern.

<Method of Manufacturing Image Pickup Apparatus>

Figure 3:
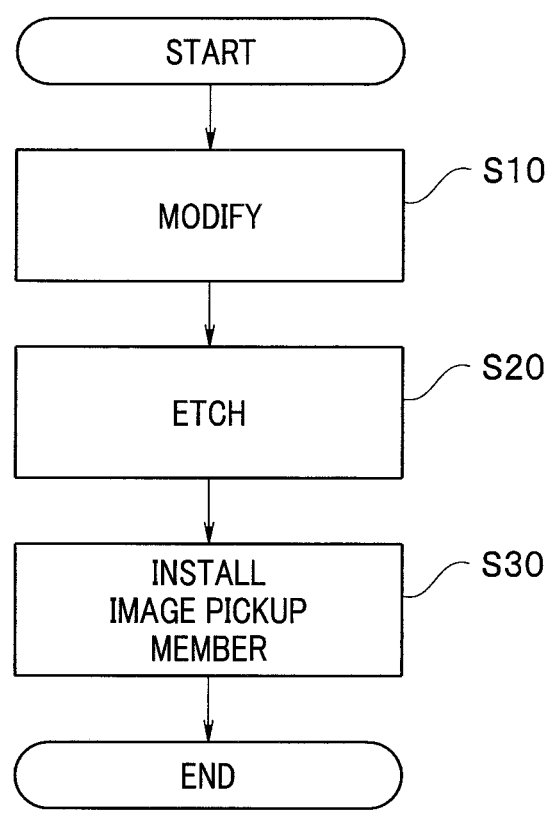
FIG. 3 is a flowchart of a method of manufacturing the image pickup apparatus according to the first embodiment.

A method of manufacturing the image pickup apparatus 1 will be described by following the flowchart illustrated in FIG. 3. In the image pickup apparatus 1, the optical member 10 is produced by cutting a glass wafer 11W including a plurality of optical members 10.

<Step S10> Modifying Step

By using a laser to modify the glass inside the glass wafer 11W that acts as the glass block, a first modified space R10 including a first path RH connected to the exit surface 10SB that acts as an exterior surface of the glass block is produced.

For the glass of the glass wafer 11W, silica glass, phosphate glass, borate glass, fluoride glass, chloride glass, sulfide glass, or one of the above glasses doped with Ge or the like is used.

Figure 4:
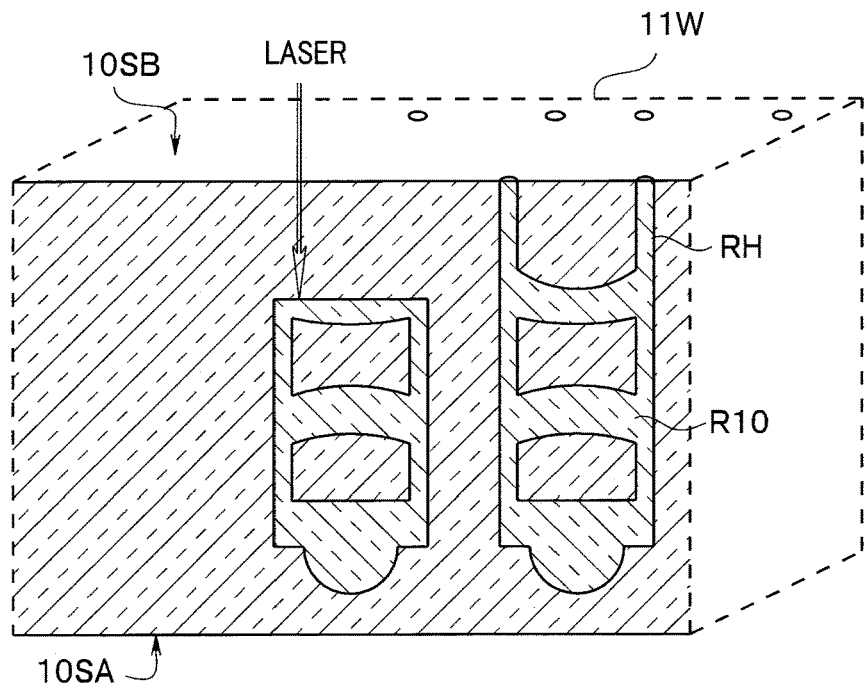
FIG. 4 is a perspective cross-sectional view for explaining the method of manufacturing the image pickup apparatus according to the first embodiment.
Figure 5:
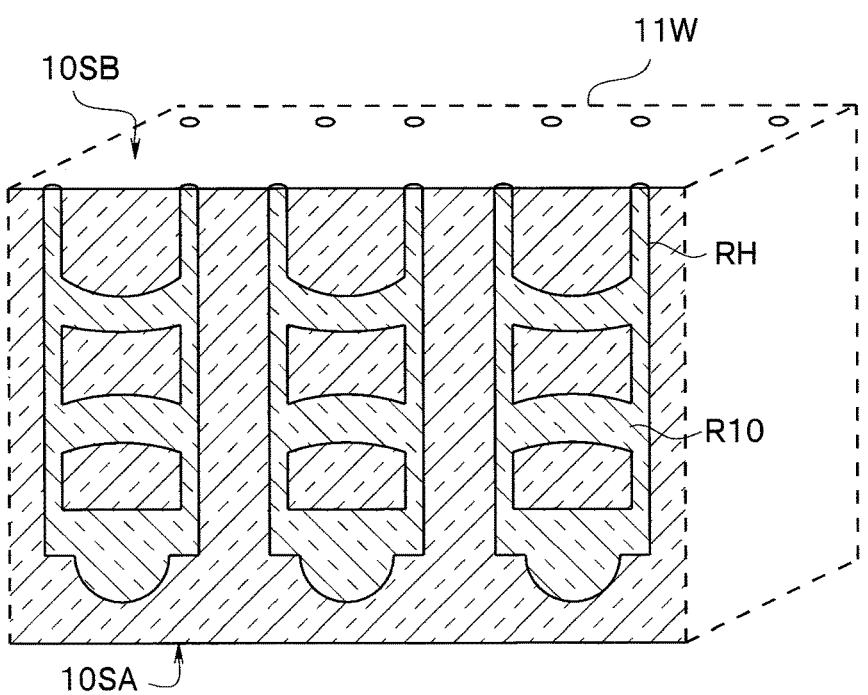
FIG. 5 is a perspective cross-sectional view for explaining the method of manufacturing the image pickup apparatus according to the first embodiment.

As illustrated in FIGS. 4 and 5, the first modified space R10 is formed using a laser modification method. For example, by using a femtosecond pulse laser having an intensity of 105 W/cm$^2$ at the focus and moving the focal point inside the glass wafer 11W, the first modified space R10 having a desired shape is formed.

A laser energy for forming a modified region is lower than the energy of laser ablation for removing material and laser irradiation for heating material, and a pulse energy is from 10 nJ to 1 µJ, for example. A frequency of the laser is from 100 kHz, to 1 MHz, and a pulse width in particular is from 100 to 500 fs.

For example, a focal point obtained by using a lens to condense laser light (pulse width 150 fs, frequency 200 kHz, wavelength 800 nm, average output 600 W) is moved along a predetermined path. Consequently, as illustrated in FIG. 5, the first modified space R10 including a first path RH connected to the exit surface 10SB is formed.

<Step S20> Etching Step

Figure 6:
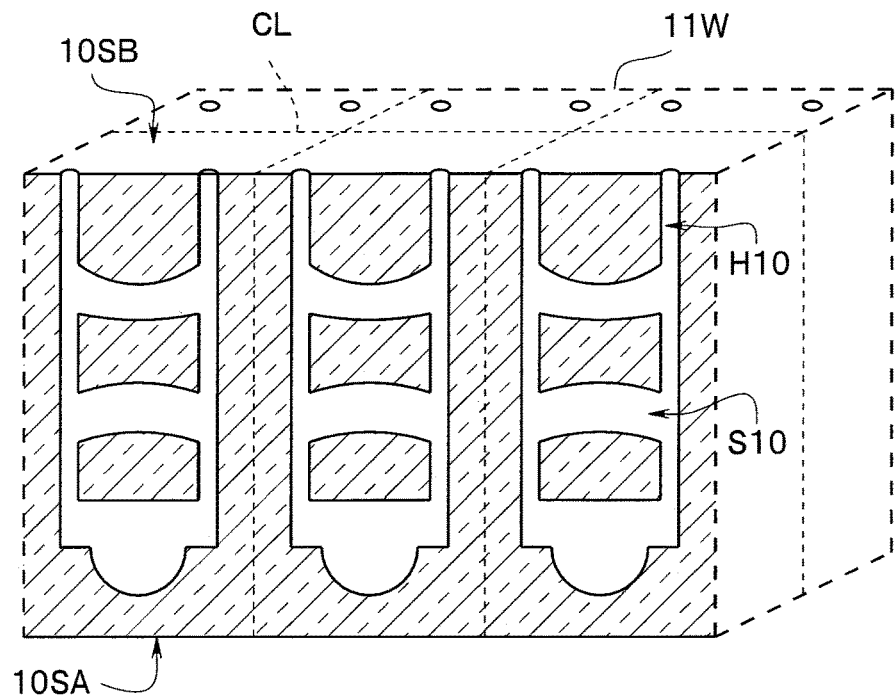
FIG. 6 is a perspective cross-sectional view for explaining the method of manufacturing the image pickup apparatus according to the first embodiment.

As illustrated in FIG. 6, by etching the first modified space R10, the optical member 10 internally including the optical space S10 connected to the first holes H10 having openings in the exit surface 10SB is produced.

For example, the glass wafer 11W including the first modified space R10 formed internally is etched using a low-concentration hydrofluoric acid solution. An etch rate of the first modified space R10 is 100 times an etch rate of an unmodified region. Consequently, only the first modified space R10 is melted to form the optical space S10.

Note that after the etching step S20, it is preferable to further provide a smoothing step that smooths the lens surface.

In the smoothing step, an etched surface is smoothed by using a hydrofluoric acid solution of even lower concentration than the hydrofluoric acid solution used in the etching step, for example.

Thereafter, the glass wafer 11W in which the plurality of optical spaces S10 are formed is cut along cutting lines CL to produce the optical member 10.

<Step S30> Image Pickup Member Installing Step

Figure 7:
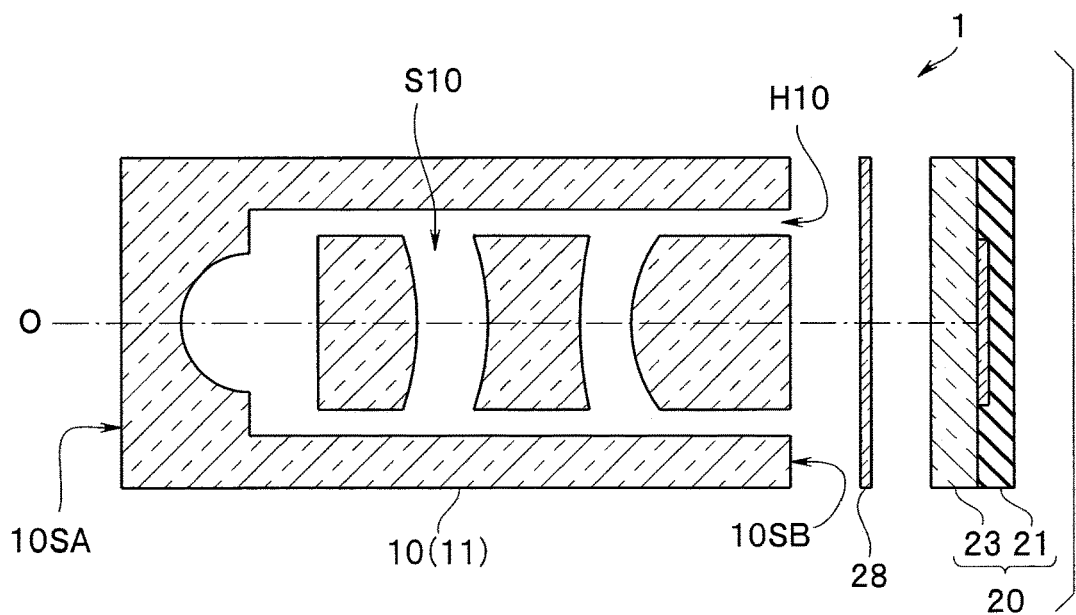
FIG. 7 is an exploded cross-sectional view for explaining the method of manufacturing the image pickup apparatus according to the first embodiment.

As illustrated in FIG. 7, the adhesive 28 is used to install the image pickup member 20 on the exit surface 10SB that acts as an exterior surface of the optical member 10. As described previously, a portion of the adhesive 28 is also disposed inside the first holes H10.

Note that the image pickup member 20 does not have to include the cover glass 23. In addition, the cutting step may also be performed after installing a plurality of image pickup members 20 on the glass block 11, In other words, the cutting step may be performed after installing a plurality of image pickup members 20 on the glass wafer 11W in which the plurality of optical spaces S10 are formed.

It is not practical to specify that the optical space S10 of the optical member 10 is formed by the process of etching the first modified space R10 formed by the laser modification method. In other words, an appropriate means of measurement and analysis to distinguish the optical space S10 formed by another method does not exist. Furthermore, we are unable to find a wording that specifies a structure or characteristic relating to a difference from the optical space S10 formed by another method.

Modifications of First Embodiment

Image pickup apparatuses 1A and 1B according to modifications of the first embodiment resemble the image pickup apparatus 1 and have the same effects, and therefore components having the same functions are denoted with the same reference signs, and description thereof is omitted.

Modification 1 of First Embodiment

Figure 8A:
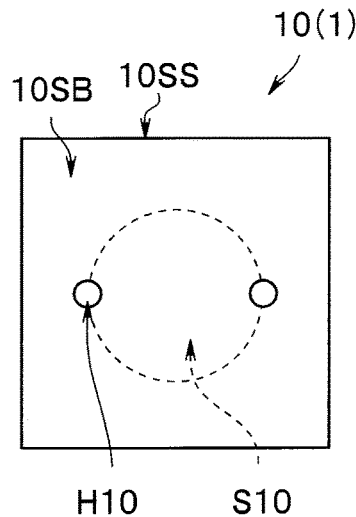
FIG. 8A is a bottom view of an optical member in the image pickup apparatus according to the first embodiment.
Figure 8B:
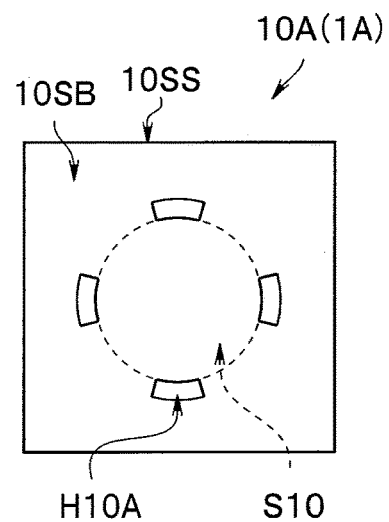
FIG. 8B is a bottom view of an optical member in the image pickup apparatus according to Modification 1 of the first embodiment.

As illustrated in FIG. 8A, two first holes H10 each having a circular opening in the exit surface 10SB are formed in the optical member 10 of the image pickup apparatus 1. However, in an optical member 10A of the image pickup apparatus 1A according to Modification 1 of the first embodiment illustrated in FIG. 8B, four first holes H10A each having an arc-shaped opening in the exit surface 10SB are formed.

It is sufficient for at least one first hole to be provided for allowing the etching solution to enter the interior of the glass wafer 11W in the etching step S20. The shape of the opening of the first holes is not limited to a circle.

Modification 2 of First Embodiment

Figure 9:
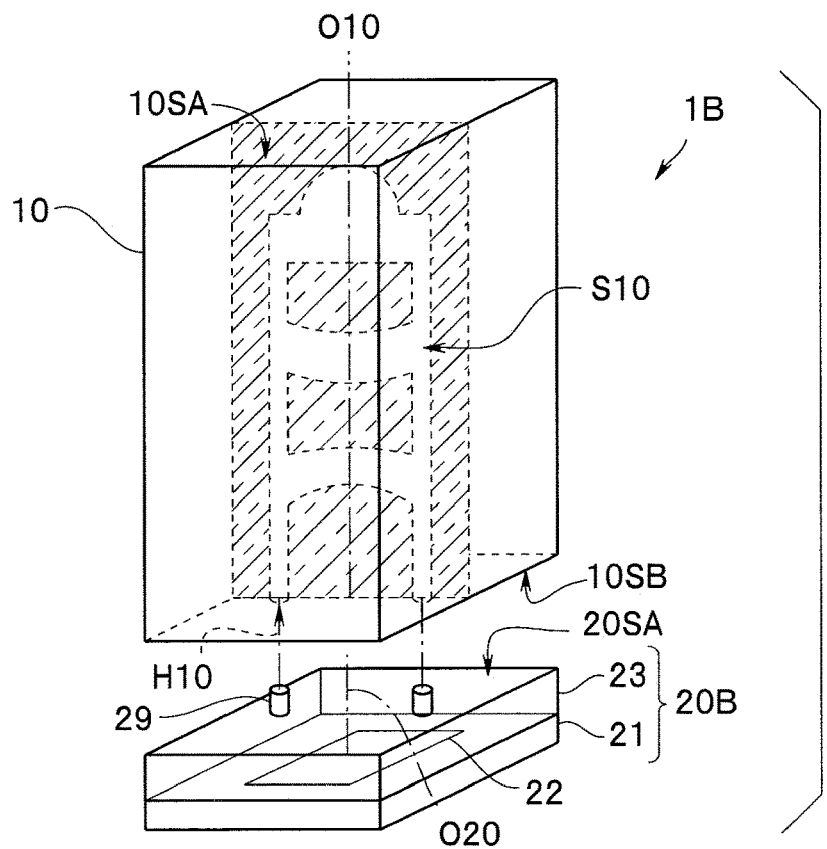
FIG. 9 is an exploded view for explaining the method of manufacturing the image pickup apparatus according to Modification 2 of the first embodiment.

As illustrated in FIG. 9, in an image pickup apparatus 1B according to Modification 2 of the first embodiment, projections 29 are provided on a surface 20SA bonded to the optical member 10 of an image pickup member 20B. For example, the projections 29 contain a resin disposed by a photolithography method or a metal disposed by a plating method. Etching may also be performed after disposing an etching mask on the cover glass 23, and unetched areas may be treated as the projections 29. Note that the adhesive 28 is not illustrated in FIG. 9 and the like.

With the method of manufacturing the image pickup apparatus 1B, in the image pickup member installing step S30, the projections 29 disposed on the image pickup member 20B are inserted into the first holes H10 disposed on the exit surface 10SB of the optical member 10.

By respectively inserting the two projections 29 into the two first holes H10, an optical axis O10 of the optical member 10 and an optical axis O20 of the image pickup member 20 are aligned. The image pickup apparatus 1B is easy to manufacture because positioning of the optical member 10 and the image pickup member 20 in the direction (in-plane direction) orthogonal to the optical axis is unnecessary. Furthermore, because the openings of the first holes H10 are closed up by the projections 29, the optical member 10 has favorable moisture resistance.

In a case where the first holes H10 and the projections 29 have a circular cross section in the direction orthogonal to the optical axis, at least two first holes H10 and at least two projections 29 are necessary for positioning. However, in cases such as where the first holes H10 and the projections 29 have a rectangular cross section or the like in the direction orthogonal to the optical axis, obviously one first hole H10 and one projection 29 are sufficient.

Second Embodiment

An image pickup apparatus 1C according to a second embodiment resembles the image pickup apparatus 1 and has the same effects, and therefore components having the same functions are denoted with the same reference signs, and description thereof is omitted.

Figure 10:
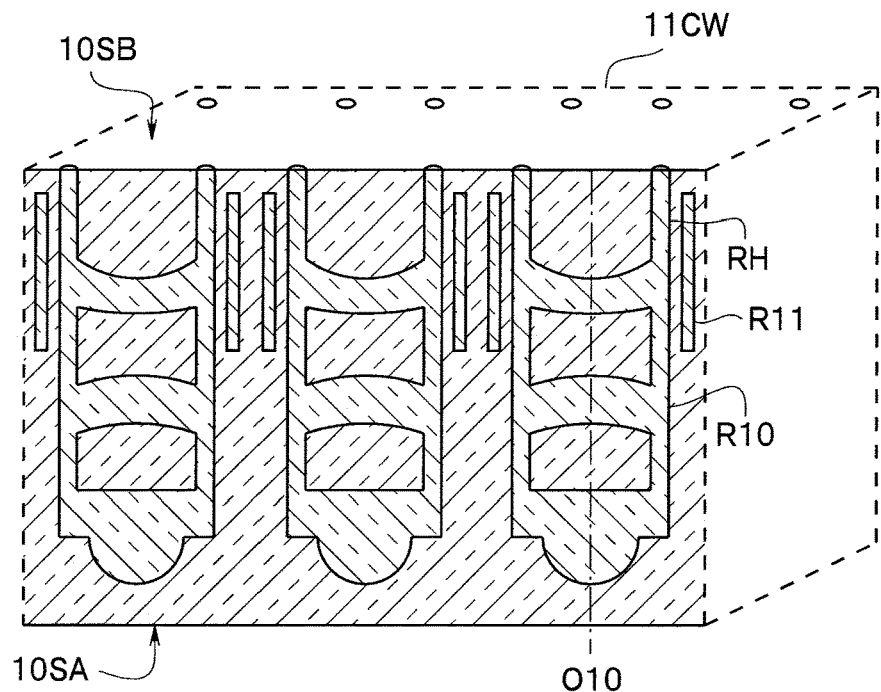
FIG. 10 is a perspective cross-sectional view for explaining the method of manufacturing the image pickup apparatus according to a second embodiment.

As illustrated in FIG. 10, with a method of manufacturing the image pickup apparatus 1C, in the modifying step S10, solid alignment marks R11, each of which is a second modified space parallel to the optical axis O10 of the optical member, are produced near the first modified space R10 that acts as the optical space in a glass wafer 11CW in which the plurality of optical spaces S10 are formed. The solid alignment marks R11 are not connected to an exterior surface. The solid alignment marks R11 having no path allowing the intrusion of an etchant are not etched in the etching step S20.

Figure 11:
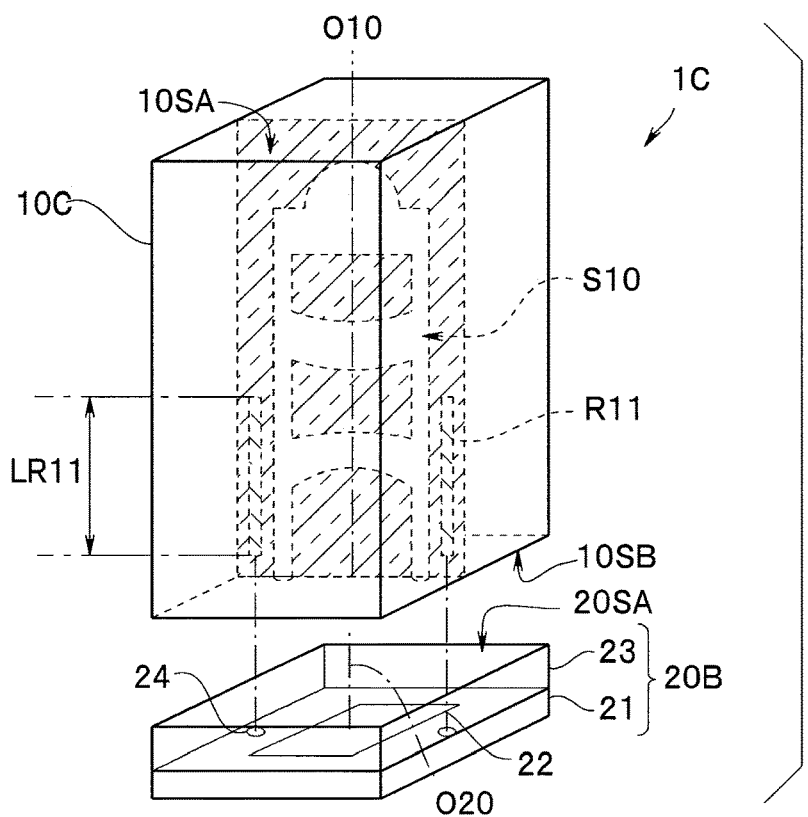
FIG. 11 is an exploded view for explaining the method of manufacturing the image pickup apparatus according to the second embodiment.

Additionally, as illustrated in FIG. 11, in the image pickup member installing step S30, the solid alignment marks R11 are used to provide an aligning step in which positioning is performed such that an optical axis O10 of an optical member 10C and an optical axis O20 of an image pickup member 20B are in a parallel state.

Figure 12A:
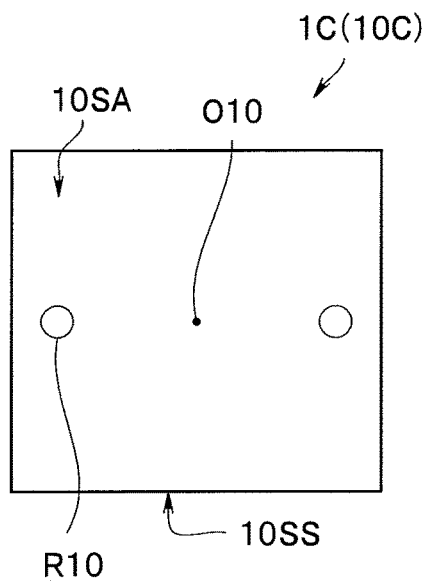
FIG. 12A is a top view of an optical member for explaining the method of manufacturing the image pickup apparatus according to the second embodiment.
Figure 12B:
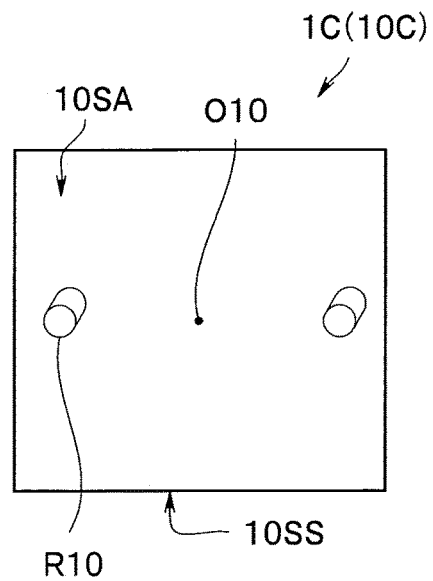
FIG. 12B is a top view of an optical member for explaining the method of manufacturing the image pickup apparatus according to the second embodiment.

As illustrated in FIG. 12A, in a case where the optical member 10C is in an upright state on the surface 20SA of the image pickup member 20B, that is, in a case where the optical axis O10 of the optical member 10C and the optical axis O20 of the image pickup member 20 are in a parallel state, the cylindrical solid alignment marks R11 parallel to the optical axis O10 appear circular when observed from the incident surface 10SA. However, as illustrated in FIG. 12B, in a case where the optical member 10C is bonded to the surface 20SA obliquely, that is, in a case where the optical axis O10 of the optical member 10C and the optical axis O20 of the image pickup member 20 are not in a parallel state, the sides of the cylindrical solid alignment marks R11 parallel to the optical axis O10 are visible.

If the image pickup member 20 is placed on a reference surface (stage) of a positioning device, the optical axis O10 of the optical member 10C is perpendicular to the reference surface. By installing the optical member 10C positioned in the upright state in accordance with the solid alignment marks R11 on the image pickup member 20, the optical axis O10 of the optical member 10C and the optical axis O20 of the image pickup member 20 are in a parallel state.

In a general positioning step, positioning is performed in the in-plane direction orthogonal to the optical axis, but by using the solid alignment marks R11, the optical axis O10 and the optical axis O20 can be disposed parallel to each other. Consequently, the image pickup apparatus 1C has particularly excellent optical characteristics. Furthermore, the solid alignment marks R11 is easy to manufacture since the solid alignment marks R11 can be produced at the same time as the first modified space R10 in the modifying step S10.

For accurate alignment, the solid alignment marks R11 preferably have a length LR11 in the optical axis direction that is at least 10% of the optical path length (the length of the optical member in the optical axis direction). Note that obviously positioning in the in-plane direction may also be achieved by aligning the solid alignment marks R11 with alignment marks 24 in the image pickup member 20.

Solid alignment marks parallel to the optical axis may also be formed by laser modification of an ordinary glass lens optical member that holds a plurality of glass lenses and an optical filter in a frame member.

The solid alignment marks R11 are not connected to an exterior surface, and consequently are not etched in the etching step S20. However, the solid alignment marks may also be connected to an exterior surface and may be marks that become spaces in the etching step S20. The spaces may also be filled with a colored resin.

Third Embodiment

An image pickup apparatus 1D according to a third embodiment resembles the image pickup apparatus 1 and has the same effects, and therefore components having the same functions are denoted with the same reference signs, and description thereof is omitted.

<Step S10> Modifying Step

Although not illustrated, with a method of manufacturing the image pickup apparatus 1D, in the modifying step S10, a second modified space including a second path not connected to the first modified space but connected to the exit surface 10SB is also produced in addition to the first modified space inside a glass block 11DW.

<Step S20> Etching Step

Figure 13:
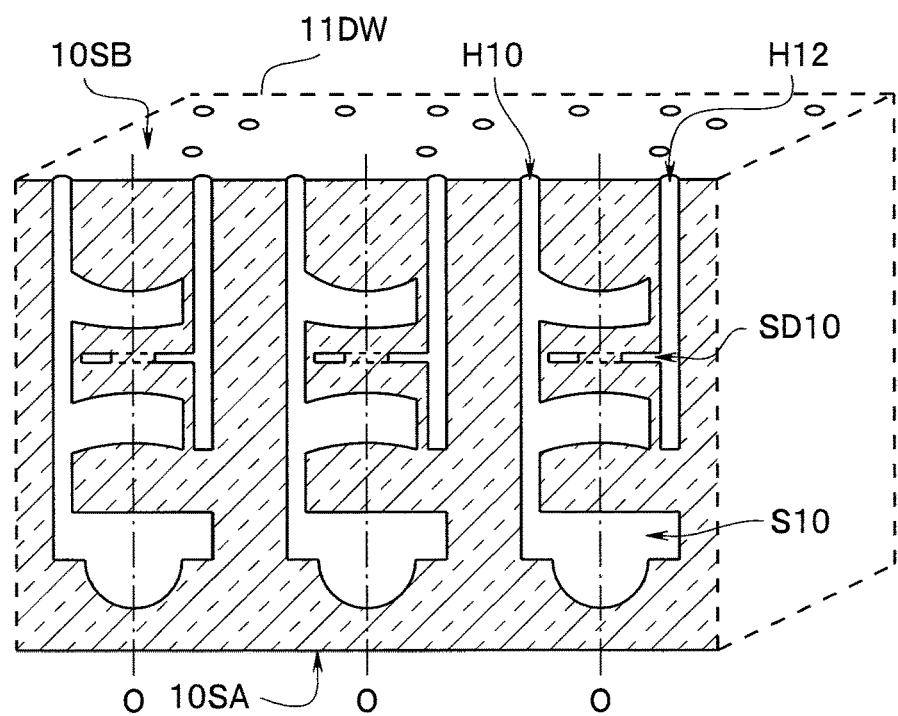
FIG. 13 is a perspective cross-sectional view for explaining the method of manufacturing the image pickup apparatus according to a third embodiment.

As illustrated in FIG. 13, in the etching step S20, an aperture space SD10 connected to a second hole H12 having an opening in the exit surface 10SB is produced in addition to the optical space S10 connected to the first holes 1110 having an opening in the exit surface 10SB in the glass block 11DW. The optical space S10 and the aperture space SD10 are not connected.

<Step S25> Filling Step

Figure 14:
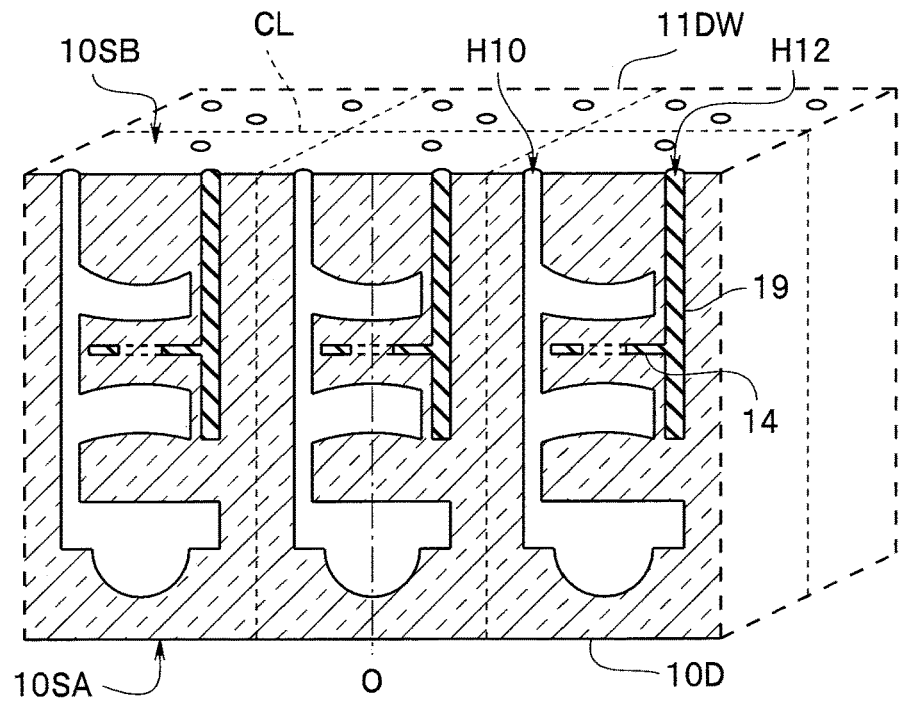
FIG. 14 is a perspective cross-sectional view for explaining the method of manufacturing the image pickup apparatus according to the third embodiment.
Figure 15:
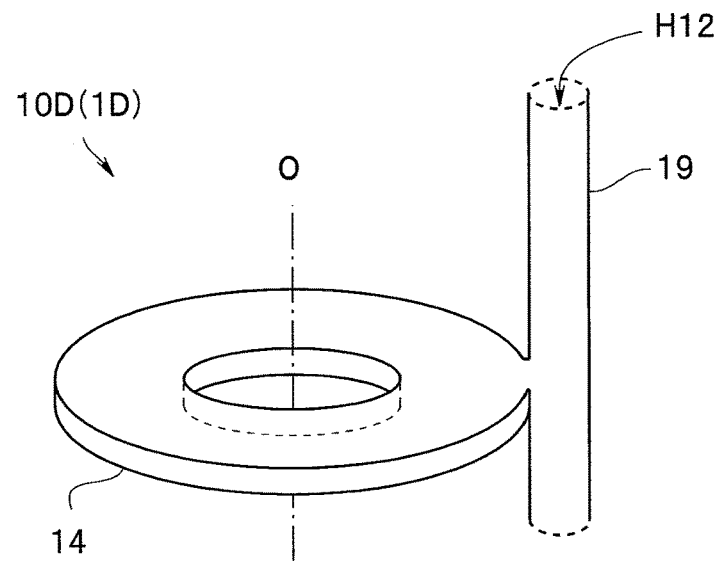
FIG. 15 is a perspective view of an aperture of an optical member in the image pickup apparatus according to the third embodiment.

Additionally, as illustrated in FIG. 14, in the filling step S25 after the etching step S20, a light-shielding material 19 is injected into the aperture space SD10 to produce an aperture 14 of an optical member 10D illustrated in FIG. 15. The light-shielding material 19 is a resin containing light-shielding particles such as carbon, for example. Note that the optical member 10D may also include a plurality of apertures 14.

Because the optical member 10D includes the aperture 14, the image pickup apparatus 1D has excellent optical characteristics.

Note that as illustrated in FIG. 15, the second hole H12 is formed parallel to the optical axis O. Consequently, the second hole H12 filled with the light-shielding material 19 may also be used as a solid alignment mark.

Fourth Embodiment

Figure 16:
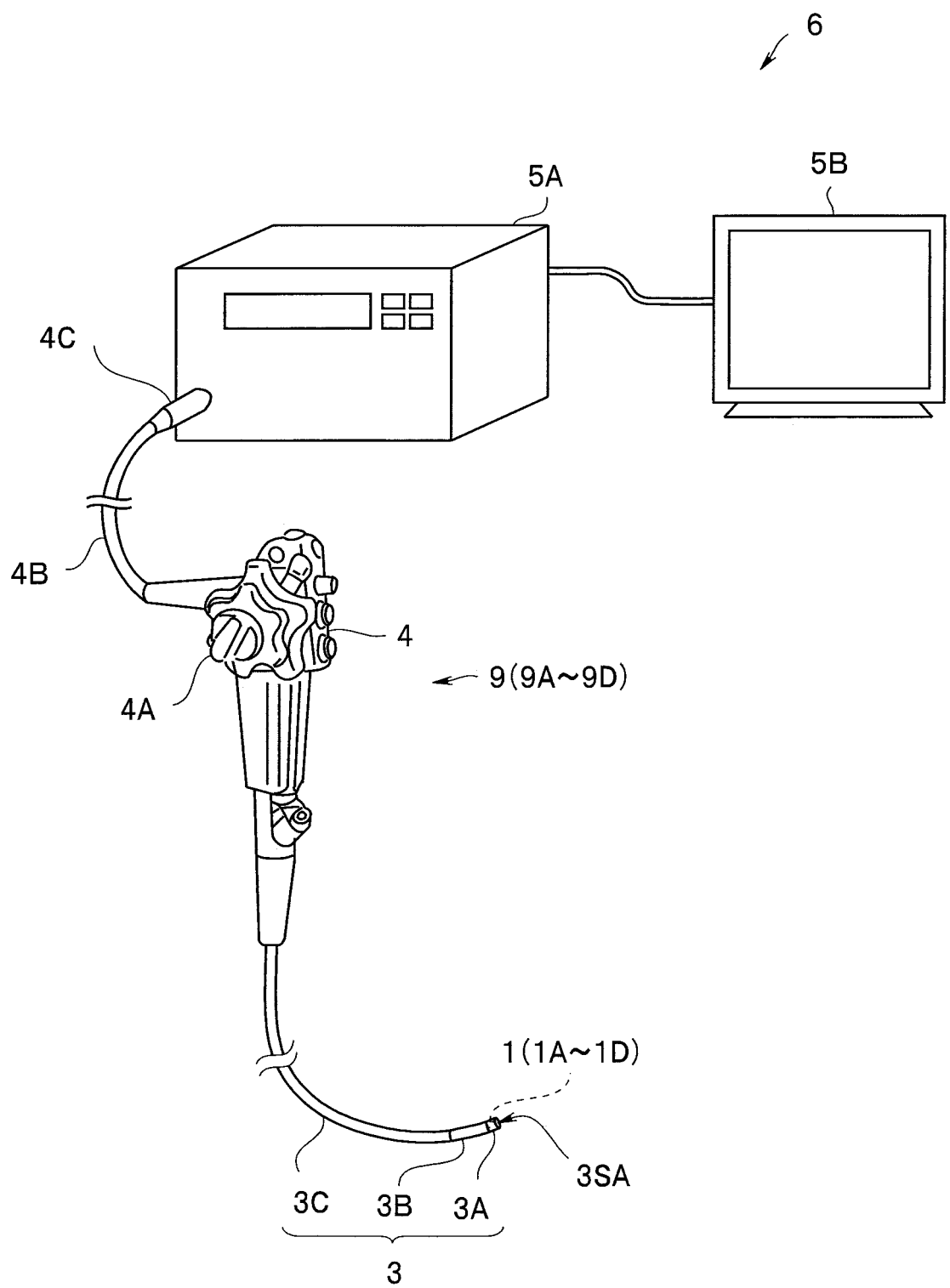
FIG. 16 is a perspective view of an endoscope according to a fourth embodiment.

As illustrated in FIG. 16, in an endoscope 9 according to the present embodiment, the image pickup apparatus 1 or 1A to 1D is installed in a distal end portion 3A of an insertion portion 3.

The endoscope 9 includes an insertion portion 3, a grasping portion 4 disposed on the side of a proximal end portion of the insertion portion 3, a universal cord 4B extending from the grasping portion 4, and a connector 4C disposed on the side of a proximal end portion of the universal cord 4B. The insertion portion 3 includes the distal end portion 3A on which the image pickup apparatus 1 or 1A to 1D is installed, a bending portion 3B extending from the proximal end side of the distal end portion 3A and bendable for changing the direction of the distal end portion 3A, and a flexible portion 3C extending from the proximal end side of the bending portion 3B. The incident surface 10SA of the image pickup apparatus 1 or 1A to 1D is exposed on a distal end surface 3SA of the distal end portion 3A. As already described, because the incident surface 10SA is one surface of a glass block and does not have openings to the first holes H10, moisture does not intrude from the incident surface 10SA. On the grasping portion 4, a rotating angle knob 4A that a surgeon uses as an operation portion for operating the bending portion 3B is disposed.

The universal cord 4B is connected to a processor 5A through the connector 4C. The processor 5A controls an endoscope system 6 as a Whole, and also performs signal processing on an image pickup signal outputted by the image pickup apparatus 1 or 1A to 1D, and outputs the signal processing result as an image signal. A monitor 5B displays the image signal outputted by the processor 5A as an endoscopic image. Note that the endoscope 9 is a flexible scope for medical use, but may also be a rigid scope or an endoscope for industrial use. In other words, the flexible portion and the like are not essential components of an endoscope according to the embodiment. The endoscope according to the embodiment may also be a capsule endoscope provided with the image pickup apparatus 1 or 1A to 1D.

Note that if the image pickup apparatuses 1B and 1C, for example, include the configuration of the image pickup apparatus 1A or the like according to a modification of the first embodiment, each obviously has the effects of the image pickup apparatus 1A or the like. Furthermore, endoscopes 9A to 9D provided with the image pickup apparatuses 1A to 1D obviously have the effects of the endoscope 9 provided with the image pickup apparatus 1, and have the effects of each of the image pickup apparatuses 1A to 1D.

The present invention is not limited to the embodiments and the like described above, and various modifications and alterations are possible without changing the gist of the present invention.

What is claimed is:

1. An image pickup apparatus manufacturing method comprising:
    modifying glass inside a glass block using a laser to produce a first modified space including a first path connected to an exterior surface of the glass block;
    modifying the glass inside the glass block using the laser to produce a second modified space including a second path not connected to the first modified space but connected to the exterior surface;
    etching the first modified space to produce an optical member that internally includes an optical space including at least one lens surface and connected to a first hole including a first opening in the exterior surface;
    etching the second modified space to produce an aperture space connected to a second hole including a second opening in the exterior surface;
    filling the aperture space by injecting a light-shielding material into the aperture space to produce an aperture of the optical member; and
    installing, on the optical member, an image sensor configured to receive a subject image formed by light condensed by the optical member;
    wherein the first opening to the first hole is not provided on an incident surface on an opposite side from an exit surface of the optical member on which the image sensor is installed.

2. The image pickup apparatus manufacturing method according to Claim 1, wherein the optical space has at least one concave lens surface and at least one convex lens surface.

3. The image pickup apparatus manufacturing method according to claim 1, further comprising smoothing the at least one lens surface after etching the first modified space.

4. The image pickup apparatus manufacturing method according to claim 1, wherein when installing the image sensor on the optical member, a projection disposed on the image sensor is inserted into the first hole formed in the exit surface on which the image sensor is installed.

5. The image pickup apparatus manufacturing method according to claim 1, wherein
when modifying the glass, solid alignment marks each containing a second modified space parallel to an optical axis of the optical member are produced near the first modified space, and
when installing the image sensor on the optical member, the solid alignment marks are used for positioning such that the optical axis of the optical member and an optical axis of the image sensor are in a parallel state.

6. The image pickup apparatus manufacturing method according to Claim 1, wherein the installing comprises applying an adhesive between the exterior surface and a corresponding surface of the image sensor.

7. The image pickup apparatus manufacturing method according to claim 1, wherein the installing comprises applying an adhesive between the exterior surface and a corresponding surface of the image sensor, the adhesive covering at least the first opening.

8. The image pickup apparatus manufacturing method according to claim 6, wherein the adhesive filling a portion of at least the first hole.

9. The image pickup apparatus manufacturing method according to claim 1, further comprising installing a cover glass on the image sensor prior to installing the image sensor on the optical member.

* * * * *